United States Patent [19]

Ryan et al.

[11] 4,327,178
[45] Apr. 27, 1982

[54] URINARY KALLIKREIN ASSAY: SPECIFIC SUBSTRATES AND ASSAY METHOD

[75] Inventors: James W. Ryan; Alfred Chung, both of Miami, Fla.

[73] Assignee: University of Miami, Coral Gables, Fla.

[21] Appl. No.: 249,645

[22] Filed: Mar. 31, 1981

Related U.S. Application Data

[63] Continuation of Ser. No. 34,930, May 1, 1979, abandoned.

[51] Int. Cl.$^3$ .......................... C12Q 1/38; C12Q 1/36
[52] U.S. Cl. ...................................... 435/23; 435/24; 260/112.5 R; 424/1.5
[58] Field of Search ................. 435/4, 13, 23, 24, 805, 435/810; 260/112.5 R; 424/1, 1.5

[56] References Cited

U.S. PATENT DOCUMENTS

| | | | |
|---|---|---|---|
| 3,983,099 | 9/1976 | Niswender | 424/1.5 |
| 4,016,042 | 4/1977 | Svendsen | 435/23 |
| 4,016,250 | 4/1977 | Saxema | 424/1.5 |
| 4,022,876 | 5/1977 | Anbar | 424/1.5 |
| 4,046,633 | 9/1977 | Keutal | 435/23 |
| 4,061,625 | 12/1977 | Ekenstam | 435/13 |
| 4,070,245 | 1/1978 | Svendsen | 435/23 |
| 4,115,374 | 9/1978 | Ryan | 435/23 |
| 4,176,009 | 1/1979 | Sakakibara | 435/24 |
| 4,177,109 | 12/1979 | Tohyama | 435/24 |

FOREIGN PATENT DOCUMENTS

2629067 1/1977 Fed. Rep. of Germany .

OTHER PUBLICATIONS

Aasen, A. O. et al., *Eur. Surg. Res.* 10, 50 (1978).
Amundsen, E. et al., Chemistry and Biology of the Kallikrein-Kinin System in Health and Disease, Pisano and Austin, Ed., DHEW Publication No. (NIH) 76-791, Washington, p. 215 (1977).
Claeson, G. et al., Haemostasis 7, 62 (1978).
Day, A. R. et al., *Agents and Actions* 6 421 (1976).
Lineweaver, H. et al., *J. Am. Chem. Soc.* 56, 658 (1934).
Morita, T. et al., *J. Biochem.* 82, 1495 (1977).
Oza, N. B. et al., *Biochem. J.* 171, 285 (1978).
Fink, "Studies on the Biological Function of Glandular Kallikrein", Proceeding of the International Symposium on Kinins, Tokyo, 1978.
Amundsen, "Methods for the Determination of Glandular Kallikrein by Means of a Chromogenic Tripeptide Substrate", Proceedings of the International Symposium on Kinins, Tokyo, 1978.

*Primary Examiner*—Ernest G. Therkorn
*Attorney, Agent, or Firm*—Irons and Sears

[57] ABSTRACT

Substrates and method for the assay of urinary kallikrein are provided. The substrates have the general formula

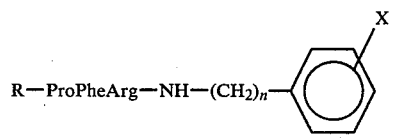

wherein
R is H, acetyl, benzoyl, cyclopentylcarbonyl, succinyl, $R_1$—$Ser_1$ or $R_1$—Phe—Ser where $R_1$ is H, acetyl, benzoyl, cyclopentylcarbonyl or succinyl,
X is H, tritium, 3-iodo or 4-iodo, and
n is 0 or 1.

Radioactive label may be incorporated in the anilide or benzylamide moiety. Hydrolysis catalyzed by urinary kallikrein yields labeled aniline or benzylamine as product.

The assay method includes mixing the enzyme with substrate in a buffered solution, pH 7.5–10.5, the substrate being present preferably at a concentration substantially below $K_m$. After incubating to allow the reaction to proceed, the reaction is terminated and the radioactive hydrolysis product is separated and counted.

Also disclosed are compounds of the type

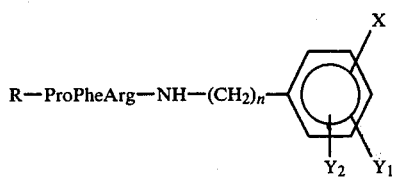
wherein R, $R_1$ and n are as defined above. X is 3—OH or 4—OH. $Y_1$ is 3-iodo if X is 4—OH or 6-iodo if X is 3—OH. $Y_2$ may be H or 5-iodo if $Y_1$ is 3-iodo, or 4-iodo if $Y_1$ is 6-iodo.
17 Claims, 2 Drawing Figures

URINARY KALLIKREIN ASSAY: SPECIFIC SUBSTRATES AND ASSAY METHOD

The government has rights in the invention pursuant to grants No. HL22087 and HL22896 from the United States Department of Health, Education and Welfare.

This application is a continuation of application Ser. No. 034,930, filed May 1, 1979 now abandoned.

BACKGROUND AND PRIOR ART

Kallikrein is an enzyme which functions physiologically in the formation of the hypotensive peptides bradykinin and kallidin by hydrolytic cleavage of the precursor peptide kininogen. The enzyme hydrolyzes peptide bonds on the carboxyl side of arginine or lysine residues and thus resembles trypsin and other proteases having a serine at the active site, such as thrombin, urokinase, and plasmin. There are two main groups of kallikreins, plasma and glandular. Urinary kallikrein has similar characteristics to a glandular kallikrein. The urinary enzyme is of special interest because it is implicated in blood pressure regulation and regulation of sodium balance. The assay of human urinary kallikrein is of clinical significance in the diagnosis of hypertension, in determining an appropriate course of treatment and in monitoring the effects of medication.

Serum and urinary kallikreins are immunologically distinguishable and have different pH optima and substrate specificities. Human urinary kallikrein is immunologically distinct from rat or dog urinary kallikrein. The enzyme is found only in minute amounts in human urine. Development of an assay for human urinary kallikrein activity requires the specific development of a suitable substrate capable of providing sufficient specificity and sensitivity. Compounds such as benzoylarginine ethyl ester and tosylarginine methyl ester, although hydrolyzed by the enzyme, are unsuitable because of the many known enzymes of trypsin-like specificity which also hydrolyze the substrates. In general, substrates whose hydrolysis is measured spectrophotometrically are unsuitable since such measurements do not provide sufficient sensitivity for convenient measurement of the minute amounts of human urinary kallikrein encountered in clinical practice.

A variety of substrates suitable for kallikrein have been discovered among peptide analogs of the C-terminal portion of bradykinin. Svendsen, U.S. Pat. No. 4,016,042 disclosed benzoyl-ProPheArg-p-nitroanilide as a substrate for spectrophotometric assay of serum kallikrein. (All amino acid residues are in the L-configuration herein, unless otherwise specified.) The following abbreviations are employed:

| Tos | Tosyl |
|-----|-------|
| Pro | Proline |
| Phe | Phenylalanine |
| Arg | Arginine |
| Ser | Serine |
| Boc | t-butoxycarbonyl |
| Aoc | amyloxycarbonyl |

Hydrolysis of the nitroanilide moiety results in a spectrophotometric change detectable where micromolar amounts of product are accumulated. However, the substrate is inactive with human urinary kallikrein, at least where present in amounts currently needed for assay.

It was suggested by Day, A. R., Chung, A. and Ryan, J. W., *Agents and Actions* 6, 421 (1976), that the compounds Boc-ProPheArg-orthohydroxyanilide and Boc-ProPheArg-p-iodoanilide could be converted into suitable radioassay substrates by [$^{125}$I] iodination of the former compound and catalytic tritiation by dehalogenation of the latter. For reasons not presently understood, however, the catalytic tritiation of the p-iodoanilide has proven to be a difficult reaction, with low yields and consequent low specific activity, under the best of circumstances.

Attention has recently focused on kallikrein substrate peptides having at least one D-amino acid in the sequence. For example, German O.S. No. 2629067 discloses derivatives of D-ProPheArg, for the assay of serum kallikrein. Substrates of this sort have been found to provide a more sensitive assay than the L-enantiomers, for the measurement of serum kallikrein. The success of the D-amino acid containing peptides has prompted further research to discover even more effective substrates.

SUMMARY OF THE INVENTION

The present invention provides specific substrates and methodology for the radioassay of mammalian urinary kallikrein. The substrates are peptide derivatives of the general form: R-ProPheArg benzylamide and R-ProPheArg anilide, where R is H, acetyl, cyclopentylcarbonyl, benzoyl, succinyl, $R_1$—Ser or $R_1$—PheSer$_1$ where $R_1$ is H, acetyl, cyclopentylcarbonyl, benzoyl or succinyl.

The substrates may be radioactively labeled by substitution of tritium or [$^{14}$C] in the anilide or benzylamide moiety, or by iodination of the anilide or benzylamide moiety with [$^{125}$I] in the 3- or 4-position. The 3-iodo and 4-iodo derivatives are also active substrates for human urinary kallikrein. The substrates are highly selective for human and other mammalian urinary kallikrein and have a very low $K_m$, a fact which is especially useful for radioassay.

Hydrolysis of the radioactively labeled substrates by human urinary kallikrein results in formation of radioactively labeled benzylamine or labeled aniline, respectively. In the assay method, the products are extracted from the reaction mixture with an aprotic solvent and counted by standard techniques. Using the substrates and assay method of the present invention, the kallikrein activity of 50 µl dialyzed human urine is readily measured in a 15 minute incubation at 37° C. As little as 5 ng of enzyme can be measured under these conditions.

DETAILED DESCRIPTION OF THE INVENTION

Figure 1:
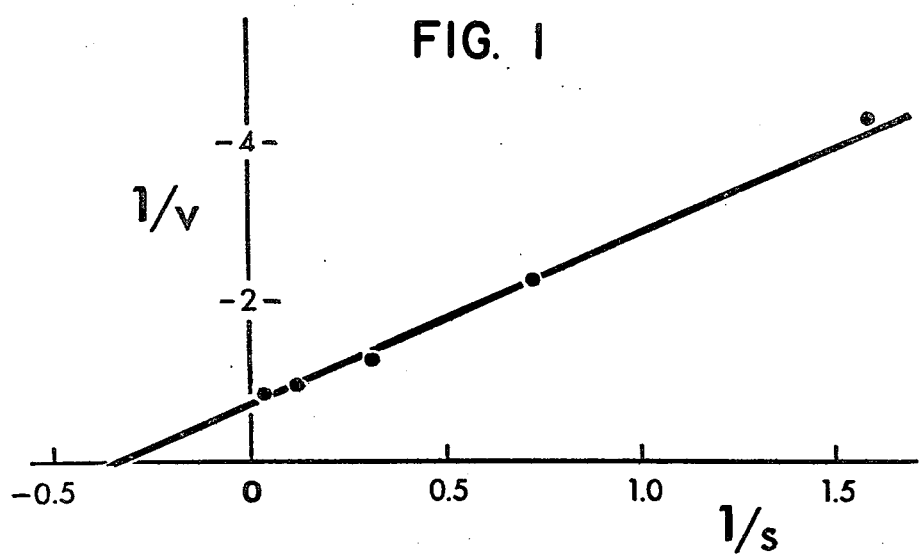

The compounds of the present invention have been discovered to be excellent substrates for human urinary kallikrein. ProPheArg-[$^3$H] anilide has a $K_m$ of approximately 0.8 µM and a $V_{max}$ of approximately 0.39 mmol/min/mg. ProPheArg-[$^3$H] benzylamide has a $K_m$ of approximately 3.0 µM and a $V_{max}$ of approximately 0.88 mmol/min/mg. The low $K_m$ renders these substrates especially suitable for a radioassay. A small amount of substrate is desirable in a radioassay, since sensitivity is maximized when the substrate has a high specific radioactivity. The specific radioactivity is a function of the proportion of labeled to unlabeled molecules in the substrate preparation. Generally, the cost of the substrate preparation will increase as the specific radioactivity is increased. Therefore, substrates that can be used at low concentration, such as those of the present invention, are advantageous. The low $K_m$ values exhibited by the substrates of the present invention are indicative of a highly specific binding between the enzyme and substrate. Such specific binding generally increases the likelihood that substrate will only be hydrolyzed by human urinary kallikrein rather than some other enzyme with trypsin-like activity, especially when substrate is present in relatively small amounts in the assay mixture.

The present substrates have the unexpected property of inhibiting human urinary kallikrein when present at concentrations greater than about 10 $\mu$M, or greater than about $3 \times K_m$. Substrate inhibition has not previously been reported for human urinary kallikrein, but may account for the previously mentioned lack of activity of the p-nitroanilide compounds with this enzyme. The latter are typically used at higher concentrations for spectrophotometric assay. The discovery of substrate inhibition with the compounds of the present invention raises the possibility of therapeutic use in reduction of excessive glandular kallikrein activity, in vivo.

According to the foregoing principles, the substrates of the present invention may be used at concentrations ranging from about 1 nM to approximately 10 $\mu$M, depending on the amount of enzyme present, and the specific activity of the substrate. Preferably, the assay is carried out using 10 nM to 40 nM substrate.

Previous attempts to synthesize the [$^3$H]-anilide compounds of the present invention by catalytic-dehalogenation of the 4-iodoanilide in the presence of [$^3$H$_2$] resulted in poor yields, at best. Surprisingly, it has been found that catalytic tritiation of the 3-iodobenzylamide provides an excellent yield of the [$^3$H]-benzylamide. Synthesis of [$^3$H]-anilides is preferably accomplished by coupling [$^3$H]-aniline with Boc-ProPheArg-(nitro), yielding substrate having a specific radioactivity of about 0.1 to 2 Ci/mmol, depending on available specific radioactivity of [$^3$H]-aniline starting material. The catalytic-[$^3$H] of 3-iodobenzylamides yields specific radioactivities on the order of 25 Ci/mmol.

It has been noted that spectrophotometric assays, such as developed for serum kallikrein, depend upon accumulation of sufficient product to produce measurable change in optical density at a chosen wavelength. Optimal substrates for such assays exhibit high $V_{max}$ values with the enzyme, and optimal reaction conditions are chosen so as to achieve a high $V_{max}$. The desirability of the D-amino acid analogs of the prior art is most likely related to an enhancement of $V_{max}$, possibly accompanied by increased $K_m$, attendant upon D-amino acid substitution. In contrast, the present substrates are composed of L-amino acids, to maximize the binding affinity of the enzyme for the substrate. High binding affinity (as manifested by a low $K_m$) permits the use of substrates at low concentration in the assay, yielding the advantages discussed, supra.

Another unexpected feature of the present substrates is the fact that unprotected derivatives (where R is H) are as effective, or more effective, than $N^\alpha$-substituted derivatives. A protecting group was previously considered essential to avoid degradation of substrate by amino peptidases. By contrast, we have now found that no significant degradation of this type occurs in the assay of urinary kallikrein, under the assay conditions employed herein.

The pH optimum for the assay of human urinary kallikrein using substrates of the present invention was found to be unusually high, with maximal activity in the range pH 9.0 to 10.0. Enzyme activity was approximately one-tenth optimal at pH 7.0 and approximately one-half optimal at pH 8.0 and pH 10.7. Above pH 10.7, there was a rapid loss of activity with increasing pH. Tris(2-amino-2-hydroxyethyl-1,3-propanediol) buffer is prepared to either Hepes (N-2-hydroxyethylpiperazine-N'-2-ethanesulfonic acid) or phosphate buffers. Accordingly, for the assay method, 0.05 M tris buffer pH 9.5 is preferred. At pH 9.5, the reaction of human urinary kallikrein with the substrates of the present invention at 37° C. for 15 minutes is linear for kallikrein in the range 20 ng/ml to 700 ng/ml. Much lower amounts of kallikrein can be measured by extending the incubation time or reducing the volume of the reaction mixture.

Human urine is treated to remove low molecular weight impurities, either by overnight dialysis against 0.9%(w/v) NaCl or by gel filtration. A typical reaction mixture may contain 50 $\mu$l dialyzed urine and 0.1 $\mu$Ci of substrate at a final concentration of 20 ng/ml buffered with 0.1 M tris-HCl, pH 9.5, in a total reaction volume of 100 $\mu$l. Reaction tubes are incubated at 37° C. for two hours. Variations of incubation time and temperature for the purpose of increasing or decreasing the amount of product formed are known expedients within the scope of ordinary skill in the art. Reactions may be stopped by any technique which causes rapid termination of the enzyme-catalyzed reaction without significant alteration of the product concentration. Use of an excess volume of base, e.g., 1.0 ml of 0.1 NaOH, is preferred. The product is separated from the reaction mixture by extraction with a measured volume of an aprotic solvent such as toluene or ether, or by other suitable means such as ion-exchange chromatography. Where solvent extraction is employed, an aliquot of the solvent (containing reaction product) may be sampled for radioactivity counting. Scintillation counting is preferred for counting tritium, and use of an extracting solvent such as toluene or ether permits direct transfer of a solvent aliquot to the scintillation fluid.

A standard curve may be constructed substituting purified kallikrein for dialyzed urine. A unit of enzyme is defined herein as that amount required to hydrolyze substrate at an initial rate of 1% per minute at 37° C. The foregoing definition is applicable where the concentration of substrate is well below $K_m$ such that hydrolysis is first order with respect to substrate concentration. The number of kallikrein units/ml of dialyzed urine is given by $$\frac{\frac{2(\text{Test c.p.m.} - \text{Blank c.p.m.})}{\text{Total Substrate c.p.m.}} \times 100}{\text{incubation time (min)} \times \text{vol. of enzyme in ml}}$$

where 1.0 ml of solvent is used for the extraction and an aliquot of 0.5 ml is taken for counting. The blank c.p.m. value is determined in a control reaction lacking enzyme but otherwise treated identically.

EXAMPLE 1

Synthesis of H-ProPheArg [$^3$H]-benzylanilide

Boc-ProPhe-OH was synthesized by conventional solution phase peptide synthesis, coupling Boc-Pro-N-hydroxy succinimide ester with Phe-benzyl ester toluene sulfonic acid salt using N-ethylmorpholine and 1- hydroxybenzotriazole. An oil product was obtained in 98% yield. The product was deprotected by hydrogenolysis in ethanol with 5% palladium on barium sulfate as catalyst. The peptide gave white crystals from ethyl acetate in 51.9% yield, m.p. 140.5°–141° C. The product behaved as a pure compound in 3 thin-layer chromatographic systems and on electrophoresis at pH 5.0. The peptide was not reactive with ninhydrin reagent but was reactive with o-tolidine/chlorine ($Cl_2$) reagents.

Aoc-Arg(Tos)-3-iodobenzylamide was prepared by coupling Aoc-Arg(Tos)—OH with meta-iodobenzylamine by using dicyclohexylcarbodiimide and 1-hydroxybenzotriazole. The coupling reaction product (m.p. 80° C.) was deprotected with ethanolic HCl to yield H-Arg(Tos)-3-iodobenzylamide. HCl.

The protected dipeptide Boc-ProPhe-OH was coupled to H-Arg(Tos)-3-iodobenzylamide. HCl in the presence of 1-hydroxybenzotriazole in dimethylformamide (DMF) with dicyclohexylcarbodiimide at about 0° C. with N-ethyl morpholine as base. The reaction yielded a foam-like material, Boc-ProPheArg(Tos)-3-iodobenzylamide. The product was deprotected by treatment with anhydrous HF to yield H-ProPheArg-3-iodobenzylamide.

The catalytic tritiation was performed essentially as follows: H-ProPheArg-3-iodobenzylamide (10 mg) was dissolved in 2.0 ml of DMF:water (1:1 by volume). To this was added 10 mg of 10%(w/w) palladium on $CaCO_3$ and 10 Ci of tritium gas. The reaction was stirred at room temperature for 4 hours, filtered, the filter washed with DMF:water, lyophilized to remove labile tritium and lyophilized again after addition of water. The product, H-ProPheArg-[$^3$H] benzylamide, was then dissolved in 25 ml water. Total radioactivity was 295 mCi, at a specific radioactivity of 25.6 Ci/mmole.

The labeled peptide was purified by chromatography on Bio-Rex 70 (trademark, BioRad laboratories, Fullerton, Calif.) using a gradient of acetic acid from 10%(v/v) to glacial. The purified compound could not be separated from authentic unlabeled ProPheArg-benzylamide in four thin layer chromatography systems nor upon electrophoresis at pH 1.9 or pH 5.0. Acid hydrolysis with 6 N HCl at 115° C. for 20 hours yielded benzylamine, proline, phenylalanine and arginine, identified by chromatography on silica gel plates eluted with $CHCl_3$-methanol-$H_2O$ (12:9:4 parts by volume) having Rf values of 0.86, 0.20, 0.48, and 0.08, respectively. 98.5% of the tritium was contained in the benzylamine fraction, and the amino acid products each contained less than 0.8% of the total radioactivity.

EXAMPLE 2

Synthesis of H-SerProPheArg-[$^3$H] benzylamide and H-PheSerProPheArg-[$^3$H] benzylamide.

Essentially, the method of Example 1 is employed except that the starting material Boc-Pro-N-OH-succinimide ester was replaced by Boc-Ser(Benzyl)Pro-N-OH-succinimide ester or Boc-PheSer(Benzyl)Pro-N-OH-succinimide ester, respectively, synthesized by standard solution phase peptide synthesis techniques. The starting materials are either coupled to a protected phenylalanine, as in Example 1, and thence to Arg-(Tos)-3-(or-4-)iodobenzylamide, in a two-step reaction, or directly to H-Phe-Arg($NO_2$)-3(or-4)-iodo-benzylamide formed by coupling H-Arg($NO_2$)-3(or -4)-iodobenzylamide with Boc-Phe-N-OH-succinimide ester. The coupling reactions are followed by standard deprotection reactions. Catalytic tritiation is performed essentially as described in Example 1.

The compounds H-SerProPheArg-3-iodobenzylamide, H-SerProPheArg-4-iodobenzylamide, H-SerProPheArg-[$^3$H]-benzylamide, H-PheSerProPheArg-3-iodobenzylamide, H-PheSerProPheArg-4-iodobenzylamide and H-PheSerProPheArg-[$^3$H]benzylamide are suitable substrates for the assay of human urinary kallikrein.

EXAMPLE 3

Synthesis of H-ProPheArg-[$^3$H]-anilide

The synthesis was achieved by the coupling of [$^3$H]-aniline (commercially available) with Boc-ProPheArg-($NO_2$)-OH. The starting compound, Boc-ProPhe-OH was made essentially as described in Example 1. The dipeptide was coupled to H-Arg($NO_2$)-benzylester.2-toluene sulfonic acid salt in the presence of 1-hydroxybenzotriazole in DMF with dicyclohexylcarbodiimide at about 0° C. with N-ethyl morpholine as base. The reaction yielded a yellow oil, Boc-ProPheArg($NO_2$)-benzylester, in 85% yield. The product behaved as a pure compound in three thin layer chromatography systems and on electrophoresis at pH 5. It was not reactive with ninhydrin reagent but was reactive with o-tolidine/chlorine reagents.

The product was saponified with 1.1 equivalents of 1 N KOH in methanol at room temperature for 1 hour. The reaction yielded a gum-like product, Boc-ProPheArg($NO_2$)-OH, in 61.5% yield. The product was homogeneous in three thin-layer systems and on electrophoresis at pH 5. The peptide was not reactive with ninhydrin but was reactive with o-tolidine/chlorine reagents.

Boc-ProPheArg($NO_2$)-OH was coupled with [$^3$H]-aniline in DMF by dicyclohexylcarbodiimide in the presence of 1-hydroxybenzotriazole at 4° C. overnight. The anilide was then deprotected with anhydrous HF and further purified by chromatography, first on Bio-Rex 70 eluted with an acetic acid gradient, 1%–50%(v/v), then on Sephadex G-10 (trademark, Pharmacia, Inc., Uppsala, Sweden) using 10%(v/v) acetic acid as eluent. The [$^3$H]-anilide was homogeneous in two thin-layer chromatography systems and on electrophoresis at pH 2. H-ProPheArg-[$^3$H]anilide is an excellent substrate for human urinary kallikrein. The enzymatic hydrolysis products are H-ProPheArg-OH and [$^3$H]aniline.

The foregoing procedure is used to synthesize H-SerProPheArg-[$^3$H]anilide and H-PheSerProPheArg-[$^3$H] anilide by coupling [$^3$H]aniline to the respective peptides. The resulting compounds are substrates for human urinary kallikrein.

EXAMPLE 4

Preparation of [$^{14}$C]-labeled substrates

The synthetic procedure of Example 3 is adapted to make [$^{14}$C] labeled substrates by substituting [$^{14}$C]-aniline for [$^3$H]aniline in the reaction. The same reaction is also used to produce [$^{14}$C]-benzylamide substrates by substituting [$^{14}$C]-benzylamine for [$^3$H]-aniline.

EXAMPLE 5

Synthesis of $^{125}$I-labeled substrates

When 3-hydroxyaniline, 4-hydroxyaniline, 3-hydroxybenzylamine or 4-hydroxybenzylamine are substituted for [$^3$H]-aniline in the synthesis procedure of Example 3, the corresponding 3-(or 4-)hydroxy anilides or benzylamines are produced. These compounds are readily iodinated with [$^{125}$I] or [$^{131}$I] by the chloramine-T method to yield the corresponding or [$^{125}$I]-OH-anilides or OH-benzylamides. These iodinated compounds are effective substrates for human urinary kallikrein. 3-(or 4-)iodo-anilines or 3-(or 4-)iodobenzylamines are available commercially. Iodination of 4-OH-anilides or benzylamides yields 3- and 3,5-iodo-derivatives. Iodination of the 3-OH anilides or benzylamides yields 6- or 4,6-iodo-derivatives.

EXAMPLE 6

N$^\alpha$-acetyl-, benzoyl-, and cyclopentylcarbonyl-derivatives of H-ProPheArg-[$^3$H]benzylamide were prepared by reacting the respective acid chlorides with the labeled peptide in dioxane and 1 M NaHCO$_3$ (1:1 by volume) buffered at pH 8.5 with 1.5 M Na$_2$CO$_3$. Succinyl-ProPheArg-[$^3$H]benzylamide was prepared using mono-N-succinimidyl succinate in 1 M NaHCO$_3$ and DMF (1:2 by volume). The acylated derivatives were purified by chromatography on Sephadex G-10 developed with 5%(v/v) acetic acid.

N$^\alpha$-acylated derivatives of H-ProPheArg-[$^3$H]anilide are prepared in the manner described, supra, for the benzylamides.

Urinary kallikrein-catalyzed hydrolysis of the cyclopentylcarbonylated and acetylated substrates proceeded at generally similar rates as for the non-acylated compounds. Benzoyl-ProPheArg-[$^3$H]benzylamide was hydrolyzed at about ½ the rate and the succinyl derivative was hydrolyzed at 1/10 the rate. The foregoing results were obtained under assay conditions optimized for the non-acylated substrate, using approximately 20 nM substrate and 60 ng purified urinary kallikrein (Oza, N. B. and Ryan, J. W., Biochem.J. 171, 285 (1978)), in 100 μl of 0.1 M tris HCl, pH 9.5, incubated at 37° C. for 15 minutes. These conditions may not be optimal for the acylated substrates. However, even under possibly suboptimal conditions, the N$^\alpha$-acyl derivatives are clearly active substrates.

EXAMPLE 7

Figure 2:
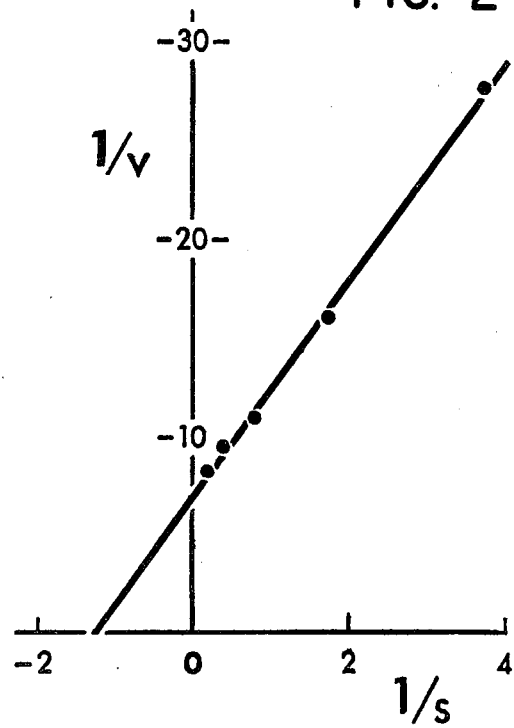

Kinetic binding constant ($K_m$) of human urinary kallikrein with H-ProPheArg-[H]benzylamide and H-ProPheArg-[$^3$H]anilide The double reciprocal plot method of H. Lineweaver and D. Burk (J.Am.Chem.Soc. 56, 658 (1934)) was used to estimate $K_m$ and $V_{max}$ for these substrates. Purified human urinary kallikrein prepared as described by Oza, N. B. and Ryan, J., supra, was used in this study. Reactions were conducted at 37° C. for 15 minutes with 62.5 ng of enzyme and the indicated amount of substrate, in 0.05 M tris-HCl pH 9.5. Reactions were terminated by the addition of a nine-fold excess of 0.1 N NaOH. The $^3$H-labeled product was separated from substrate by extraction with an equal volume (1 ml) of toluene. A 0.5 ml aliquot of the toluene phase was transferred to a scintillation vial containing a toluene-based scintillation fluid and counted. Results for H-ProPheArg-[$^3$H]-benzylamide are shown in FIG. 1, and for H-ProPheArg-[$^3$H]anilide in FIG. 2. The units of 1/v were nmol$^{-1}$ min. Units of 1/S were μmole$^{-1}$.liter. For H-ProPheArg-[$^3$H] benzylamide, $K_m$ was measured as 3.0 μM and $V_{max}$ was 0.88 mmol/min/mg protein. For H-ProPheArg-[$^3$H]-anilide, $K_m$ was 0.8 μM and $V_{max}$ was 0.39 mmol/min/mg protein.

EXAMPLE 8

Relative activity of halogenated substrates

Unlabeled halogenated 4-iodoanilide substrates, prepared essentially as described in Example 5, were compared with respect to reaction rate with human urinary kallikrein in a standard assay. Each substrate, 150 nmol, was incubated with purified human urinary kallikrein in 0.7 ml of 0.05 tris-HCl, pH 8.1 at 37° C. At timed intervals, 100 μl of reaction mixture was added to 1.0 ml of 0.1 N NaOH. The resulting solution was extracted with CHCl$_3$ and the organic phase was evaporated to dryness. The residue was dissolved in buffer and examined spectrophotometrically in the 240–300 nm range, where a difference spectrum between substrate and product is measureable. The results are shown in Table 1, with rates of hydrolysis expressed as nmol/min/mg enzyme.

TABLE 1

RELATIVE AFFINITY OF HALOGENATED SUBSTRATES FOR HUMAN URINARY KALLIKREIN

| Substrate | Rate of Hydrolysis |
|---|---|
| Phe—Arg—4-iodoanilide | Nil |
| Pro—Phe—Arg—4-iodoanilide | 0.73 |
| Ser—Pro—Phe—Arg—4-iodoanilide | 0.62 |
| Phe—Ser—Pro—Phe—Arg—4-iodoanilide | 1.12 |

EXAMPLE 9

Reaction specificity

The hydrolysis of H-ProPheArg-[$^3$H]benzylamide by a series of serine proteases was measured. Reactions were carried out using 20 nM substrate in 0.1 M tris-HCl buffer, pH 7.5 or pH 9.5, at 37° C. for 15 minutes in the presence of varied amounts of enzyme. The results are shown in Table 2, expressed as the amount of enzyme necessary to hydrolyze 10% of the substrate under the given conditions. "No hydrolysis" is used to denote no measureable reaction with a maximum of 0.5 mg/ml enzyme.

TABLE 2

SPECIFICITY STUDIES: HYDROLYSIS OF PRO—PHE—ARG—[$^3$H]BENZYLAMIDE BY SERINE PROTEASE ENZYMES

| Enzyme | pH | Amount of Enzyme Required for 10% Hydrolysis |
|---|---|---|
| Human Urinary Kallikrein | 9.5 | 45 ng (10 nM) |
|  | 7.5 | 265 ng |
| Plasmin | 9.5 | 30,600 ng |
|  | 7.5 | 17,200 ng |
| Trypsin | 9.5 | 1,030 ng |
|  | 7.5 | 400 ng |
| α-Chymotrypsin | 9.5 | No hydrolysis |
|  | 7.5 |  |
| Urokinase | 9.5 | No hydrolysis |
|  | 7.5 |  |
| Thrombin | 9.5 | No hydrolysis |
|  | 7.5 |  |

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

We claim:

1. A composition for the assay of mammalian urinary kallikrein comprising a human urinary kallikrein substrate having the formula

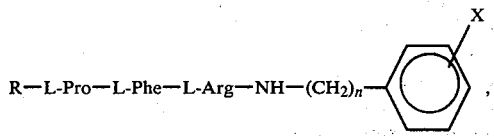

wherein
R is hydrogen, acetyl, benzoyl, cyclopentanecarbonyl, succinyl, $R_1$—L—Ser or $R_1$—L-Phe-Ser where $R_1$ is hydrogen, acetyl, benzoyl, cyclopentanecarbonyl or succinyl;
X is hydrogen, tritium, 3-iodo or 4-iodo; and,
n is 0 or 1;
and suitable buffer in the pH range 7.5–10.5.

2. A composition according to claim 1 wherein the buffer pH range is 8.5–10.5.

3. A composition according to claim 1 wherein the buffer pH range is 9.0–10.0.

4. A composition according to claim 3 wherein R is hydrogen, L—Ser or L—Phe—L—Ser; X is hydrogen or tritium, and n is 0.

5. A composition according to claim 3 wherein R is H, X is H or tritium, and n is 0.

6. A composition according to claim 3 wherein R is hydrogen, L—Ser or L—Phe—L—Ser; X is hydrogen or tritium, and n is 1.

7. A composition according to claim 3 wherein R is H, X is H or tritium, and n is 1.

8. An inhibitor composition of human urinary kallikrein comprising a compound having the formula

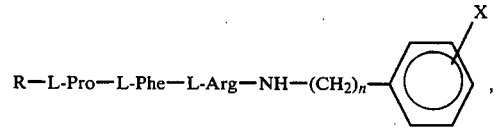

wherein
R is hydrogen, acetyl, benzoyl, cyclopentanecarbonyl, succinyl, $R_1$—L—Ser or $R_1$—L—Phe—L—Ser where $R_1$ is hydrogen, acetyl, benzoyl, cyclopentanecarbonyl or succinyl;
X is hydrogen, tritium, 3-iodo or 4-iodo; and,
n is 0 or 1;
said compound being present with the kallikrein at a concentration greater than 10 μM in a suitable buffer in the pH range 7.0–10.5.

9. A method for the assay of human urinary kallikrein comprising:
mixing said kallikrein with a substrate compound having the formula

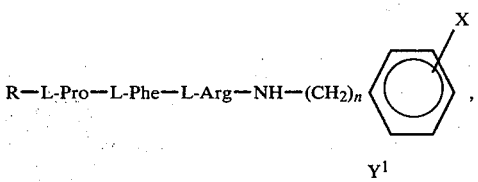

wherein
R is hydrogen, acetyl, benzoyl, cyclopentanecarbonly, succinyl, $R_1$—Ser, or $R_1$—Phe-Ser where $R_1$ is hydrogen, acetyl, benzoyl, cyclopentanecarbonyl or succinyl;
X is hydrogen, tritium, 3-iodo or 4-iodo; and,
n is 0 or 1;
at least a portion of the molecules of said substrate having a [$^3$H], [$^{14}$C] or [$^{125}$I]]substituted for the $C_1$, H or I atoms in that portion of the substrate connected by amide linkage to the carboxy group of the arginine moiety, said substrate being present at a concentration less than 10 μm in a buffer having a pH in the range 7.5–10.5;
incubating the kallikrein with the substrate to permit kallikrein-catalyzed hydrolysis thereof;
terminating the kallikrein-catalyzed hydrolysis;
separating the hydrolysis product from the substrate; and,
measuring the amount of product formed by counting the radioactivity thereof, whereby an assay of the kallikrein activity is obtained.

10. The method of claim 9 wherein the buffer has a pH in the range 8.5–10.5.

11. The method of claim 9 wherein the hydrolysis is terminated by addition of an excess of 0.1 N NaOH.

12. The method of claim 9 wherein the hydrolysis product is separated by extracting the reaction mixture with an aprotic solvent.

13. The method of claim 12 wherein the buffer has a pH in the range 9.0–10.0, the hydrolysis is terminated by adding an excess of 0.1 N NaOH and the aprotic solvent is toluene.

14. A composition for the assay of mammalian urinary kallikrein comprising a urinary kallikrein having the formula

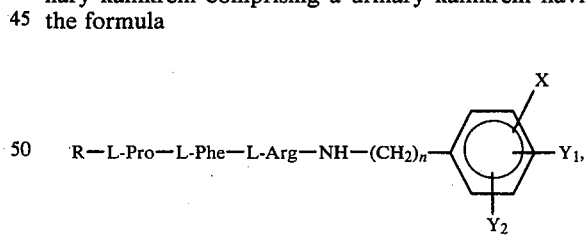

wherein
R is hydrogen, L—Ser or L—Phe-L—Ser;
n is 0 or 1;
x is 3-hydroxy or 4-hydroxy;
$Y_1$ is 3-iodo if X is 4-hydroxy or 6-iodo if X is 3-hydroxy; and,
$Y_2$ is hydrogen or 5-iodo if $Y_1$ is 3-iodo or 4-iodo if $Y_1$ is 6-iodo;
and a suitable buffer in the pH range of 7.5–10.5.

15. The composition of claim 14 wherein at least a portion of said iodo-substituents are [$^{125}$I] or [$^{131}$I] and the buffer in the pH range of 8.0–10.0.

16. A method for the assay of urinary kallikrein comprising:

mixing said kallikrein with a substrate having the formula

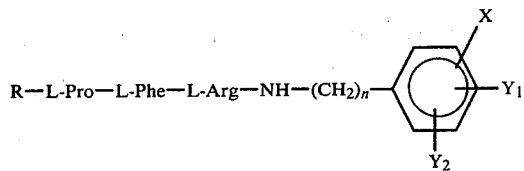

wherein
R is hydrogen, L—Ser or L—Phe-L—Ser;
n is 0 or 1;
X is 3-hydroxy or 4-hydroxy;
$Y_1$ is 3-iodo if X is 4-hydroxy or 6-iodo if X is 3-hydroxy; and,
$Y_2$ is hydrogen or 5-iodo if $Y_1$ is 3-iodo and 4-iodo if $Y_1$ is 6-iodo;
at least a portion of the molecules of said substrate having a [$^{125}$I] or [$^{131}$I] substituted for the I atoms in that portion of the substrate connected by amide linkage to the carboxy group of the arginine moiety, said substrate being present at a concentration less than 10 uM in a buffer having a pH in the range of 7.5–10.5;
terminating the kallikrein-catalyzed hydrolysis;
separating the hydrolysis product from the substrate; and,
measuring the amount of product formed by counting the radioactivity thereof, whereby an assay of the kallikrein activity is obtained.

17. The method of claim 16 wherein the hydrolysis is terminated by addition of an excess of 0.1 N NaOH, the hydrolysis product is separated by extracting the reaction mixture with an aprotic solvent, and the buffer has a pH in the range of 9.0–10.0.

* * * * *

UNITED STATES PATENT AND TRADEMARK OFFICE
CERTIFICATE OF CORRECTION

PATENT NO. : 4,327,178
DATED : April 27, 1982
INVENTOR(S) : James W. Ryan et al.

It is certified that error appears in the above-identified patent and that said Letters Patent is hereby corrected as shown below:

Column 4, line 9, "pared should read -- ferred --.

Column 7, line 5, before "or" should read -- $[^{131}I]$ --.

Signed and Sealed this

Twenty-fourth Day of May 1983

[SEAL]

Attest:

DONALD J. QUIGG

Attesting Officer     Acting Commissioner of Patents and Trademarks